United States Patent
Sullivan et al.

(10) Patent No.: US 11,400,238 B2
(45) Date of Patent: Aug. 2, 2022

(54) PEN NEEDLE HUB WITH A PATIENT CONTACT SURFACE

(71) Applicant: Embecta Corp., Andover, MA (US)

(72) Inventors: Sean Sullivan, Ridgewood, MD (US); David Huang, Hayward, CA (US); Brendon Hill, Haworth, NJ (US); Sudarsan Srinivasan, Hawthorne, NJ (US); Christopher Rini, Raleigh, NC (US); Richard Klug, Roxboro, NC (US); Bruce Clyde Roberts, Hillsborough, NC (US); Didier Morel, Meylan (FR); Ronald J. Pettis, Cary, NC (US)

(73) Assignee: Embecta Corp., Andover, MA (US)

( * ) Notice: Subject to any disclaimer, the term of this patent is extended or adjusted under 35 U.S.C. 154(b) by 126 days.

(21) Appl. No.: 16/711,969

(22) Filed: Dec. 12, 2019

(65) Prior Publication Data

US 2020/0114093 A1    Apr. 16, 2020

Related U.S. Application Data

(62) Division of application No. 15/547,189, filed as application No. PCT/US2016/015680 on Jan. 29, 2016, now Pat. No. 10,569,031.

(Continued)

(51) Int. Cl.
*A61M 5/46* (2006.01)
*A61M 5/34* (2006.01)
*A61M 5/32* (2006.01)

(52) U.S. Cl.
CPC ............ *A61M 5/46* (2013.01); *A61M 5/3202* (2013.01); *A61M 5/3293* (2013.01); *A61M 5/34* (2013.01); *A61M 5/343* (2013.01); *A61M 5/349* (2013.01)

(58) Field of Classification Search
CPC .......... A61M 5/46; A61M 5/34; A61M 5/343; A61M 5/349
See application file for complete search history.

(56) References Cited

U.S. PATENT DOCUMENTS 4,040,421 A    8/1977 Young
4,125,588 A    11/1978 Hansen et al.
(Continued)

FOREIGN PATENT DOCUMENTS

CN    102395396 A    3/2012
JP    S53-142088 A    12/1978
(Continued)

OTHER PUBLICATIONS

Chinese Office Action dated Apr. 2, 2021, which issued in the corresponding Chinese Patent Application No. 201680001274.X, including Eng. translation.
(Continued)

*Primary Examiner* — Amber R Stiles
(74) *Attorney, Agent, or Firm* — Greenberg Traurig, LLP; David J. Dykeman; Roman Fayerberg

(57) ABSTRACT

A needle-bearing hub for a pen needle is provided with a distal patient-facing side having an enlarged surface for contact with the subject's skin. The enlarged surface is provided with a radius of curvature that increases the likelihood that the needle reaches full injection depth when an injection is performed at an inclined angle with respect to the surface of the skin and with to the desired depth less discomfort to the patient.

26 Claims, 14 Drawing Sheets

Related U.S. Application Data

(60) Provisional application No. 62/109,826, filed on Jan. 30, 2015.

(56) References Cited

U.S. PATENT DOCUMENTS

| | | |
|---|---|---|
| 6,843,781 B2 | 1/2005 | Alchas et al. |
| 2003/0050602 A1 | 3/2003 | Pettis |
| 2007/0005017 A1* | 1/2007 | Alchas .............. A61M 5/14244 604/117 |
| 2009/0069753 A1 | 3/2009 | Ruan et al. |
| 2009/0069755 A1 | 3/2009 | Horvath |
| 2012/0071835 A1 | 3/2012 | Marshall et al. |
| 2012/0109052 A1 | 5/2012 | Wei et al. |
| 2015/0297837 A1 | 10/2015 | Schraga |
| 2017/0197039 A1 | 7/2017 | Shiozaki et al. |

FOREIGN PATENT DOCUMENTS

| | | |
|---|---|---|
| JP | H08-299440 A | 11/1996 |
| JP | 2004-504891 A | 2/2004 |
| JP | 2004305749 | 11/2004 |
| JP | 2006-517129 A | 7/2006 |
| JP | 2009-90098 A | 4/2009 |
| JP | 2009-090098 A | 4/2009 |
| JP | 2009101140 A | 5/2009 |
| JP | 2012-519546 A | 8/2012 |
| JP | 2012519546 | 8/2012 |
| JP | 2012-523876 A | 10/2012 |
| JP | 2012-529322 A | 11/2012 |
| JP | 2013138879 | 7/2013 |
| JP | 5385260 B2 | 10/2013 |
| WO | 2002/009797 A1 | 2/2002 |
| WO | 02100467 A2 | 12/2002 |
| WO | 20020100467 A2 | 12/2002 |
| WO | 2010/119271 A1 | 10/2010 |
| WO | 2010/142813 A1 | 12/2010 |
| WO | 2012085579 A2 | 6/2012 |
| WO | 20120085579 A2 | 6/2012 |
| WO | 2015/186792 A1 | 12/2015 |
| WO | 2016123494 A1 | 8/2016 |

OTHER PUBLICATIONS

Japanese Official Notice of Rejection dated Aug. May 26, 2020, which issued in the corresponding Japanese Patent Application No. 2018-539309, including English translation.

Supplementary European Search Report dated Aug. 6, 2018, which issued in the corresponding European Patent Application No. EP 16 74 4187.2.

International Search Report and Written Opinion dated Apr. 25, 2016 which issued in PCT Application No. PCT/JP2016/015680.

European Communication which issued in corresponding Patent Application No. 14867037.5.

International Preliminary Report on Patentability and Written Opinion dated Aug. 1, 2017, which issued in the corresponding PCT Patent Application No. PCT/JP2016/015680.

* cited by examiner

PEN NEEDLE HUB WITH A PATIENT CONTACT SURFACE

This application claims the benefit of U.S. application Ser. No. 15/547,189, filed on Jul. 28, 2018, which claims the benefit under 35 U.S.C, § 371 of PCT/US2016/015680 filed on Jan. 29, 2016, which claims the benefit under 35 U.S.C. § 119(e) of U.S. Provisional Application No. 62/109,826 filed Jan. 30, 2015, which are hereby incorporated by reference in their entirety.

BACKGROUND OF THE INVENTION

Field of the Invention

The invention is in the field of medical devices. Specifically the invention is directed to a pen needle having a needle-bearing hub with a patient-contacting surface for improved injection performance. The patient contacting surface is configured for promoting the desired depth of penetration of the cannula into the skin. The inventive hub may be installed on a medication pen used to administer self-administered medications, but is not limited to use with such devices.

Description of the Related Art

A medication pen for delivering self-administered medications generally comprises a pen body, which houses a medication compartment, and a separate pen needle which may be attached to and detached from the pen body. The pen needle includes a needle-bearing hub having a recess on the proximal side for receiving the pen body and a proximal (non-patient end) needle accessing the medication compartment, typically piercing the septum of a medication cartridge in the pen body. The distal (patient-end) of the pen needle assembly includes the beveled distal end of the needle that is inserted into the injection site.

Injections may be performed in the intradermal (ID) region, the subcutaneous (SC) region and the intramuscular (IM) region. For many types of injectable medications, including insulin, the SC region is preferred for administering an injection. See, for example, Lo Presti, et al., Skin and subcutaneous thickness at injecting sites in children with diabetes: ultrasound findings and recommendations for giving injection, *Pediatric Diabetes* (2012).

Different length needles, and with increasing frequency, shorter needles such as 4 mm and 5 mm needles, are adapted to achieve injection to a specified target depth in a subcutaneous region. The present invention addresses the need to ensure that a needle is inserted to its target depth, regardless of the angle at which the user may approach the injection site with the medication pen.

In certain prior art pen needles the cannula is supported in an axially positioned post on the hub. The post forms a narrow portion extending distally from the relatively wider portion in which the pen body is received. In other pen needles known in the art, a distal face of the hub placed against the injection site may be relatively large, and may be provided with a slight taper at the edge. However, the edge of the hub engages the skin when the cannula is inserted at an angle, interfering with the injection. The slight taper is not functional during an injection, or is only at the edge of the distal face of the hub, generally having a radius of curvature greater than about 16.0 mm.

While the prior devices are generally suitable for the intended use, there is a continuing need for improved devices for controlling the penetration of a cannula for delivering a drug or medicament.

SUMMARY OF THE INVENTION

The present invention is directed to an injection device and particularly to a needle hub for coupling to an injection pen where the needle hub has skin contact surface configured for controlling the depth of penetration by a cannula extending from the needle hub. The invention is particularly directed to a needle hub device where the contact surface has a height and width that complement each other to control the depth of penetration of the cannula.

These and other objects of the invention are achieved in one aspect of the invention with a pen needle comprising, a needle-bearing hub having a recess on a proximal side for receiving a medication pen body; a cannula having a beveled distal end for injection into a subject's skin, and a proximal end for positioning in a medication compartment of the pen body, wherein the hub has a distal face having a diameter in a range of 3.0 mm to 9.5 mm; and at least a portion of the distal face has a radius of curvature in a range of 3.0 mm to 16.0 mm. In embodiments a central portion of the hub surrounding the cannula has a diameter in a range of 0.5 mm to 9.0 mm.

In another aspect, the invention is a medication pen comprising a pen body having a medication compartment with a removable pen needle having a needle hub. The needle hub has in various embodiments of the invention can have a convex distal axial surface for contacting the skin during needle insertion and drug delivery. The needle hub can have a contact surface area of about 5-50 $mm^2$. The contact surface in one embodiment can have a height of about of 0.3 to 0.7 mm and an inner ring with a surface area of 1-4 $mm^2$.

One feature of the invention is to provide an injection device with a skin contact surface having a convex surface with a height of about 0.5 to 6.0 mm and cannula for penetrating the skin projecting from the contact surface. The cannula can be located in the center of the contact surface so that the contact surface surrounds the cannula. In one embodiment the invention, the convex contact surface has a height of about 0.5 to 1.0 mm and width of about 5.0 to 7.0 mm to provide sufficient surface area and a suitable shape and angle with respect to the axis of the cannula to contact the skin and provide the controlled depth of penetration by the cannula into the skin.

Another feature of the invention is to provide an injection device having a cannula for penetrating the skin and where the device has a skin contact surface having a substantially convex surface with a width and height to control the depth of penetration. The convex surface has a height and a width to control the deformation of the skin during the insertion of the cannula to inhibit the cannula from penetrating the skin to a depth deeper than intended while ensuring the penetration to the desired depth.

In another aspect, the invention is a method to reduce an incidence of shallow injections in a program of injections, comprising administering a series of injections using the medication pen and pen needle described above.

A convex curved hub design, as described herein, provides a greater surface area contacting an injection site on a patient while minimizing injection performance issues compared to the prior devices. Specifically, greater patient comfort and stability are achieved as a result of a larger surface area contacting the skin during injection, but if an injection is performed at an angle, the edge of the hub according to present design will enable and promote full insertion of the pen needle cannula. These considerations are particularly important with pen needles having shorter cannula in a range of 4 mm or 5 mm. With shorter needles, if the needle does not penetrate the skin properly, the injection may be performed in the ID layer of the skin. Insulin and other diabetes related drugs are often preferably delivered to the SC space. If full insertion of the needle does not occur, insulin may not be delivered to the proper location. Another concern is that if the injection is too shallow, a depot of liquid may be created just below the skin surface. This depot can result in the appearance of a bulge in the skin, which may be painful or distracting to the patient or even result in leakage from the injection site. The problem of depot formation is exacerbated by a shallow injection and/or a larger volume of drug to be delivered which occur more frequently with the smaller needle lengths and larger volumes that are now used more frequently. Thus, a further object of the invention is to provide a pen needle hub that will position the cannula to deliver medication to the desired injection depth regardless of the angle of injection.

It will be understood that each of the preferred or optional features of the various embodiments may be combined with other features and features described in combination with one or more particular features may also be combined with one or more other features of the other embodiments.

These and other features of the invention will become apparent from the following detailed description of the invention, which in conjunction with the drawings disclose various embodiments of the invention.

BRIEF DESCRIPTION OF THE DRAWINGS

The following is a brief description of the drawing in which.

DETAILED DESCRIPTION OF THE INVENTION

Figure 1:
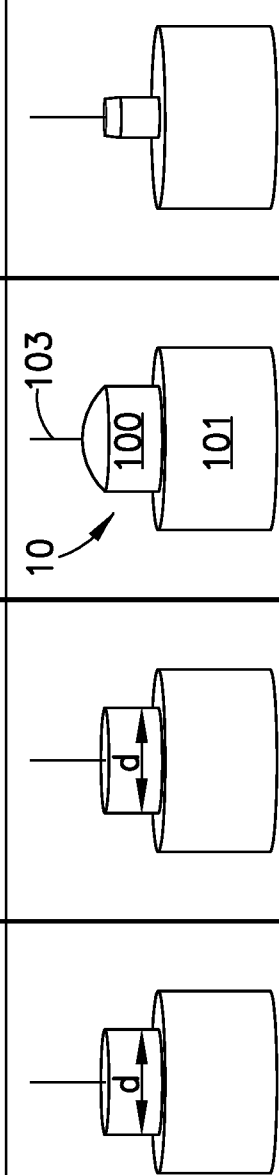
FIG. 1 depicts a needle bearing hub designs according to an embodiment of the pen needle, and comparative examples.

A "medication pen" is used herein to refer to a device having a medication compartment, typically containing multiple doses of medication, and a separate pen needle. The phrase "pen needle" refers to a needle-bearing assembly which can be attached to the medication pen body so that a proximal end of the pen needle assembly accesses a medication compartment and a distal end is adapted for insertion into an injection site to perform one or more injections. The terms "needle" and "cannula" are used herein interchangeably to refer to a thin tubular member having a sharpened or beveled end for insertion into an injection site on a subject. As used herein, the "distal" direction is in the direction toward the injection site, and the "proximal" direction is the opposite direction. "Axial" means along or parallel to the longitudinal axis of the needle and the "radial" direction is a direction perpendicular to the axial direction.

The position of the subcutaneous layer in a subject's tissue and the desired injection depth vary depending on the age of the patient, the part of the body where the injection is administered, etc. Therefore, an injection depth in absolute terms cannot be considered a critical aspect of the invention. However, as general guidance, the intradermal (ID) layer in adults has a thickness of around 2 to 3 mm, so that ID injection depth is in a range of about 0 to 3 mm, depth being measured from the outer surface of the skin. The subcutaneous (SC) region thickness can vary widely depending on the location of the injection site on the subject's body and the subject's body mass index (BMI). The average thickness of the SC space is in the range of about 7 mm to about 12 mm, so that SC injection depth is in a range of about 3 to 15 mm. The SC region may be further subdivided into the shallow subcutaneous (SSC) layer, having a thickness of about 1 mm, and an injection depth of about 2 to about 4 mm, the SC layer having a thickness of about 4 mm, at a depth of about 3 to 7 mm, and the deep subcutaneous (DSC) layer, having a thickness of about 4 mm, and a depth of about 7 to about 12 mm. If injections from a device occur in the upper region of the subcutaneous space (SSC), it is more likely that an ID injection will occur with that device. If injections from a device occur in the deeper regions of the subcutaneous space (DSC), it is more likely that an IM injection will occur with that device. Insulin is preferably delivered to the SC space.

Injections to either the ID or intramuscular (IM) space may result in different uptake of insulin from what is prescribed.

The position of different regions and layers in the tissue of different subjects may be ascertained using ultrasound imaging. These techniques also may be used to determine the location of a medication depot after injection for an empirical determination whether a particular injection was "shallow," (i.e., the depot is found at less than a predetermined optimal depth). These observations in turn may be used to verify that the number of shallow injections is reduced. If an injection is intended to be deposited in the SC region, a "shallow injection" is defined as an injection in which the depot is in the SSC or ID region.

The invention is directed to an injection device having a cannula with a predetermined length for penetrating the skin to a predetermined penetrating depth. The injection device has a skin contact surface for contacting and deforming the skin when the cannula penetrates the skin to assist in controlling the depth of penetration at various angles of injection with respect to the surface of the skin. The contact surface has a predetermined shape, width and height to control the depth of penetration into the skin to the desired layer of the skin. It has been found that the penetration force with a device having a small narrow skin contact surface of about 3 mm or less forms a deep indentation in the skin around the cannula when the device is pressed against the skin during use. The indentation formed in the outer surface of the skin often results in the cannula penetrating deeper into the skin to skin layers deeper than intended by the user. By way of example, a 4.0 mm cannula mounted in a post having a width of about 3 mm can result in the contact surface forming a concave depression in the surface of the skin so that the cannula can penetrate the deeper than 4 mm and penetrate the deeper layers of the skin that can cause pain or discomfort to the user. The deeper penetration can also cause the cannula to deliver the drug to layers of the skin that are less effective in delivering the drug to the patients.

The skin contact surface of the pen needle device surrounding the cannula has a width and height configured for providing greater control of the depth of penetration by the cannula. In one embodiment of the invention, the pen needle device is configured to obtain a cannula penetration of about 4 mm. The skin contact surface is further configured to control the shape, width and depth of deformation of the skin surface when the device is pressed against the skin during the penetration of the cannula. The width is determined as being the surface area that contacts the skin during the insertion of the cannula and during the injection or delivery of the drug using a normal insertion force. The height refers to the linear distance between the outer peripheral edge of the contact surface and the proximal end of the contact surface.

The skin contact surface of the device in one embodiment has a surface area for contacting the skin of about 5.0 mm$^2$ to about 70.0 mm$^2$ surrounding the cannula. In various embodiments, the skin contact has a surface area of about 15 mm$^2$ to 60 mm$^2$. In one embodiment, the contact surface can have a surface area of about 45-55 mm$^2$. The skin contact surface in the embodiments shown has a substantially circular or substantially circular shape with the cannula located along the center axis of the circular skin contact surface. The cannula in this embodiment has a length of about 4.0 mm to about 6.0 mm to penetrate the skin to a depth and skin layer for delivering the drug, and particularly insulin, to the most efficient depth of the skin.

The skin contact surface has a convex shape forming a continuous and uniform curvature extending from the outer edge of the hub to the distal end or outermost portion of the contact surface of the hub and the cannula so that the skin contact surface has a substantially semispherical or dome shape that contacts the skin during penetration of the cannula and delivery of the drug. The convex surface of the skin contact area can have a width or diameter of greater than 3.0 mm and typically about 6.0 to 8.0 mm and a height of about 0.5 to about 1.5 mm measured from the outer peripheral edge of the contact surface to the outermost center portion of the contact surface surrounding the cannula and spaced axially from the peripheral edge. In one embodiment the convex skin contact surface has a height of about 1.0 mm and a diameter of about 7.0 mm. The convex surface can have a radius of curvature of 6.0 to 16.0 mm. In various embodiments of the invention, the convex surface has radius of curvature of 6.0 to 9.0 mm. In other embodiments, the convex surface can have a radius of curvature of 6.0 to 7.0 mm. In one embodiment, the convex contact surface has a radius of curvature equal to or greater than the diameter of the contact surface. The radius curvature can be about 1 to 1½ times the diameter of the contact surface.

The ratio of the diameter (D) to the height (H) of the contact surface influences the depth of penetration of the cannula on insertion into the skin. Generally, the larger the ratio provides more surface area that will contact the skin and greater control of the depth of penetration. A smaller ratio D:H provides a smaller surface area that can compress the skin on insertion and result in a deeper penetration of the cannula. In certain embodiments, the ratio of the diameter to the height of the surface area can range from about 2:1 to 10:1. In other embodiments the ratio can range from about 5:1 to 8:1.

In one embodiment of the invention, the skin contact surface of the injection device has a hemispherical shape with an annular recess in the contact surface surrounding the cannula. The recess in one embodiment has a depth that enables the skin to contact the bottom of the recess when the device is pressed against the skin during the insertion of the cannula into the skin. The depth and width or diameter of the recess can be configured to form part of the contact surface to control the deformation of the skin surface during penetration of the cannula to control the depth of penetration. The recess can have a depth of about 0.4 to 1.0 mm and typically about 0.5 mm. The recess can be defined by an outer ring at the outer peripheral edge of the hub and the cannula or by an outer ring at the peripheral edge and a post or inner ring around the cannula at the center of the contact surface. In other embodiments, the recess formed in the skin contact surface can have a volume of about 0.4 to 3.0 µl.

FIG. 1 shows a comparison of the exemplary needle hub devices where 1A and 1B have a substantially flat distal surface. As shown in the exemplary embodiment of 1C in FIG. 1, pen needle hub 10 has a needle bearing hub with a proximal portion 101 enclosing a recess on a proximal side of the hub for receiving a medication pen body. Cannula 103, having a beveled distal end for injection into a subject's skin, extends from a distal face 100 on a distal portion of the hub 10. Within the distal portion, cannula 103 may be supported axially in a post (not shown), using adhesive or other means known in the art for immobilizing the needle. The proximal end of the needle is positioned in the hub for accessing the medication compartment of the pen body. The medication compartment is typically a container having a septum that can be pierced by the proximal end of the needle when the pen needle is installed on the pen.

The distal face of the hub 10 generally has a diameter between 3.0 mm and 10.0 mm. Preferably the diameter is greater than 4.0 mm, more preferably greater than 5.0 mm, and still more preferably, 6.5 mm or greater. It has been found that a relatively large surface area contacting the skin affords a more stable and comfortable injection with less compression of the skin, as compared to the prior device shown in 1D of FIG. 1, in which the patient-end cannula extends directly from a supporting narrow post on the hub. In the device shown in ID, when a patient performs an injection, the supporting post can press into the skin causing pain and discomfort, and may lead to a deeper than desired injection. Increasing the surface area of the hub that contacts the skin during an injection should lead to the subject experiencing less pain and discomfort and a more consistent injection depth. Thus, the lower limit of the diameter of the distal face is larger than the diameter of a supporting post (typically 2.7 mm). The upper end of the range for the diameter "d" of the distal face is selected so that the edge of the distal face does not interfere with injection performance. A diameter "d" greater than 9.5 mm may not provide an added benefit.

In addition to increased surface area, at least a portion of the distal face of the hub according to the invention is curved outwardly to form a convex surface. The curved portion has a radius of curvature in a range of 3.0 mm to 16.0 mm, and preferably 6 mm to 8 mm. In one embodiment, the curved portion has a radius of curvature of about 7 mm.

The entire distal face need not be curved. For example, an area adjacent the cannula having a diameter of 0.5 mm to 7 mm may be flat, i.e., perpendicular to the axis of the needle, and an area adjacent the flat area and including the peripheral edge of the distal face may have a convex curvature. The curvature at the edge of the distal face allows a needle approaching an injection site at an angle to be reoriented with respect to the injection site to penetrate more deeply, whereas the edge of a distal hub having insufficient curvature on an edge (such as shown in 1A and 1B) may prevent the needle from penetrating into the injection site when the edge of the distal face of the hub engages the skin proximate the injection site. This can cause a lateral force against the cannula that can cause the cannula to bend by the insertion force.

Figure 2:
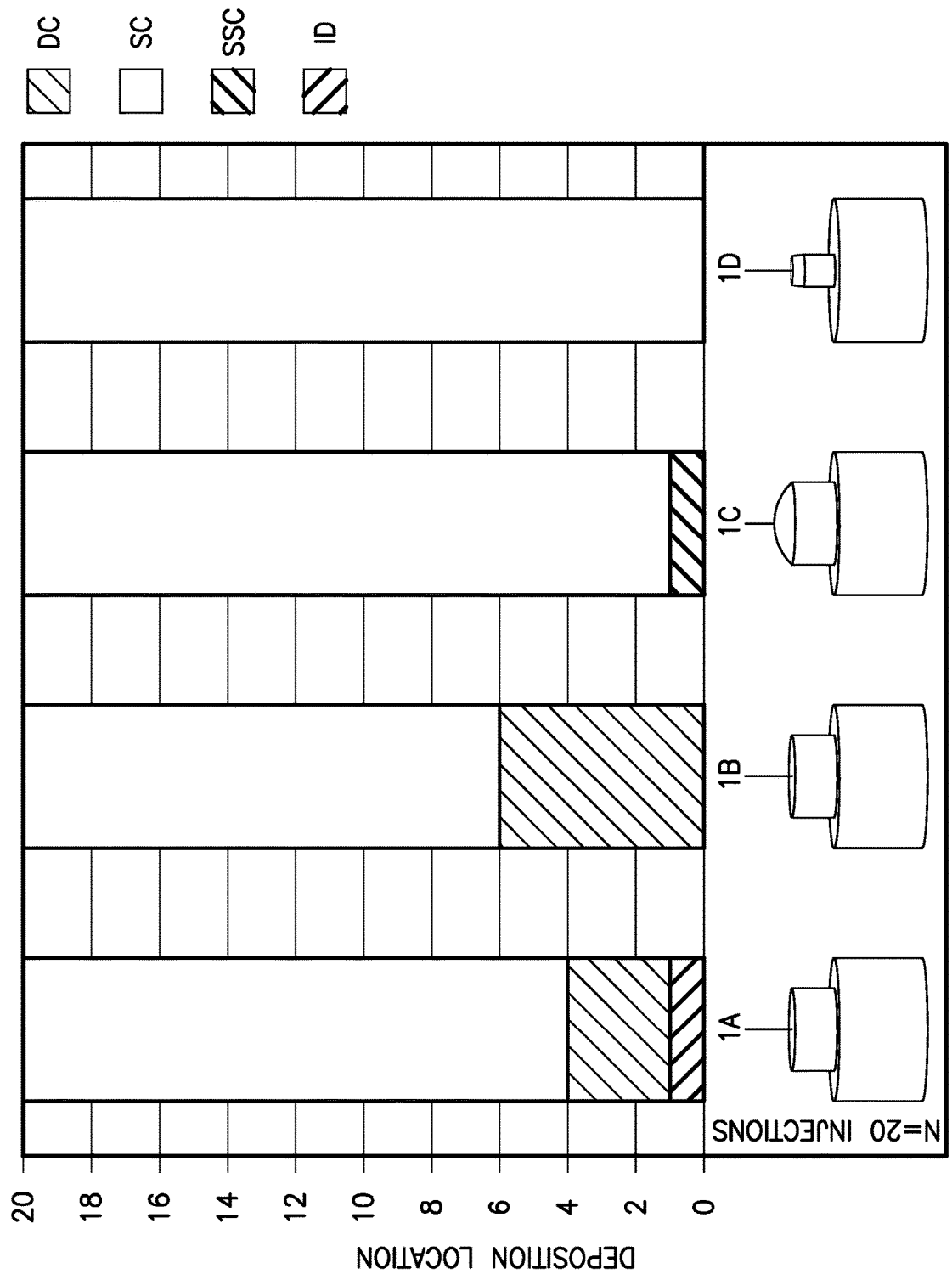
FIG. 2 depicts the results of a study showing the incidence of shallow injection using pen needle hubs described in FIG. 1.

FIG. 2 depicts the results of in vivo tests performed to determine whether the incidence of shallow (ID and SSC) injections was reduced using a hub having an enlarged distal face with curvature. FIG. 2 shows the number of shallow (ID and SSC) injections obtained with each of the hubs, demonstrating that providing a relatively large curvature to the hub face results in fewer shallow injections. Twenty injections were performed at an angle of 50 degrees with respect to a line perpendicular to the injection site. An ideal injection is performed at 0 degrees, i.e., perpendicular to the injection site. Ultrasound imaging was used to identify the depth of the medication deposition. The prior device where the cannula extends from a post (1D) did not result in shallow injections and resulted in the cannula penetrating deeper than desired. All twenty of the injections were in the SC region. Of the hubs having an enlarged distal face, 1A through 1C, the curved face resulted in fewer shallow injections.

FIG. 1 shows the hub designs used to perform injections in the in vivo test. Designs 1A and 1B included a distal face having an enlarged surface area (6.5 mm and 8.5 mm diameter, respectively) but no curvature. An embodiment according to the invention, FIG. 1C is provided with a 6 mm curvature on the distal face except for a small area around the needle. A commercial embodiment according to the prior art was also included: in which the needle is provided on a post.

Figure 3:
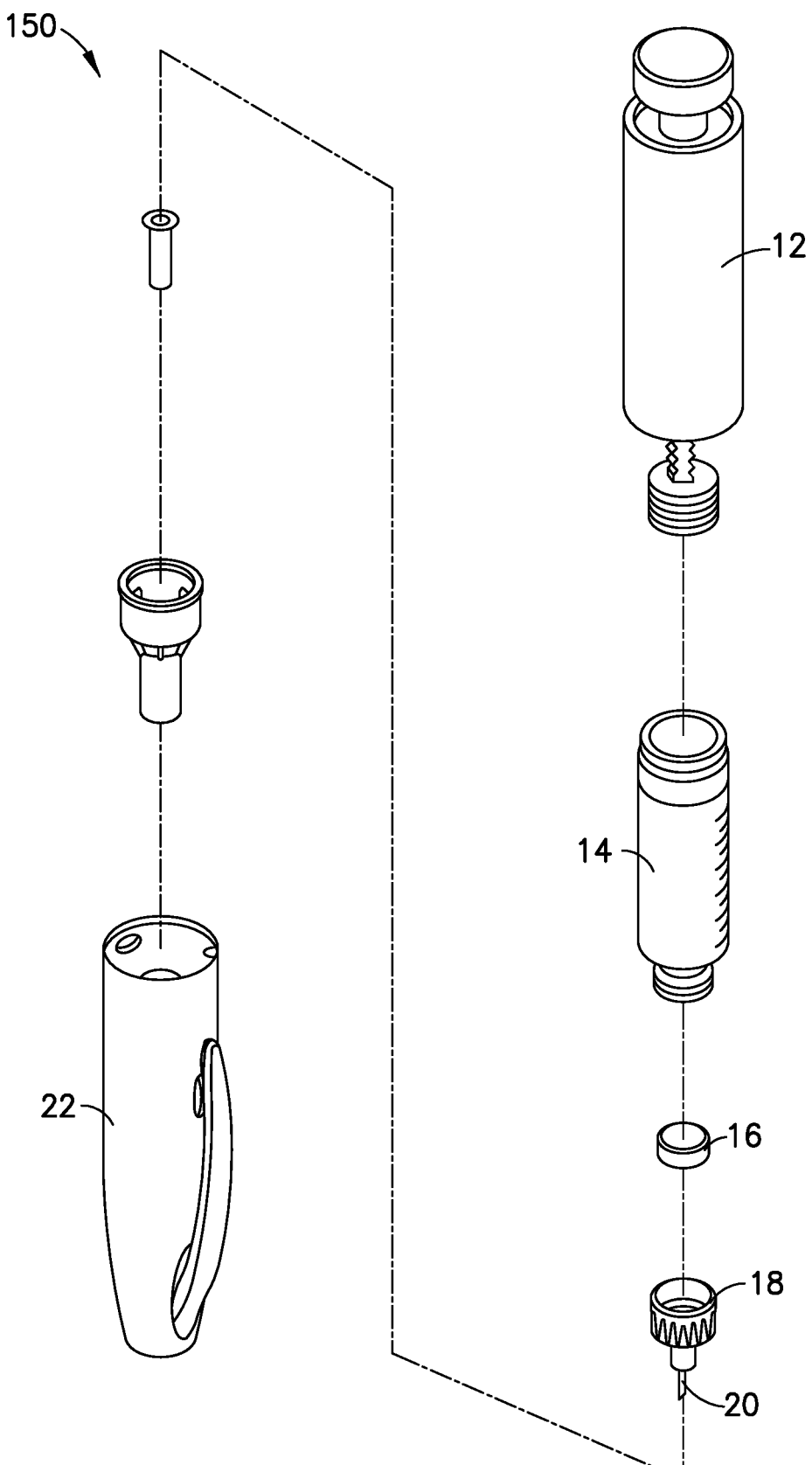
FIG. 3 is a perspective view of a pen needle assembly for use with the hub assembly of the pen needle.

Referring to FIG. 3 the injection device includes drug delivery pen 150 having an outer sleeve 12, a medicament cartridge 14 sealed by a septum 16 and a cap 22. A hub 18 having a cannula 20 is coupled to the delivery pen. A plunger is provided on the end of the cartridge to dispense the drug. The delivery pen has a structure and operation similar to those known in the art.

Figure 4:
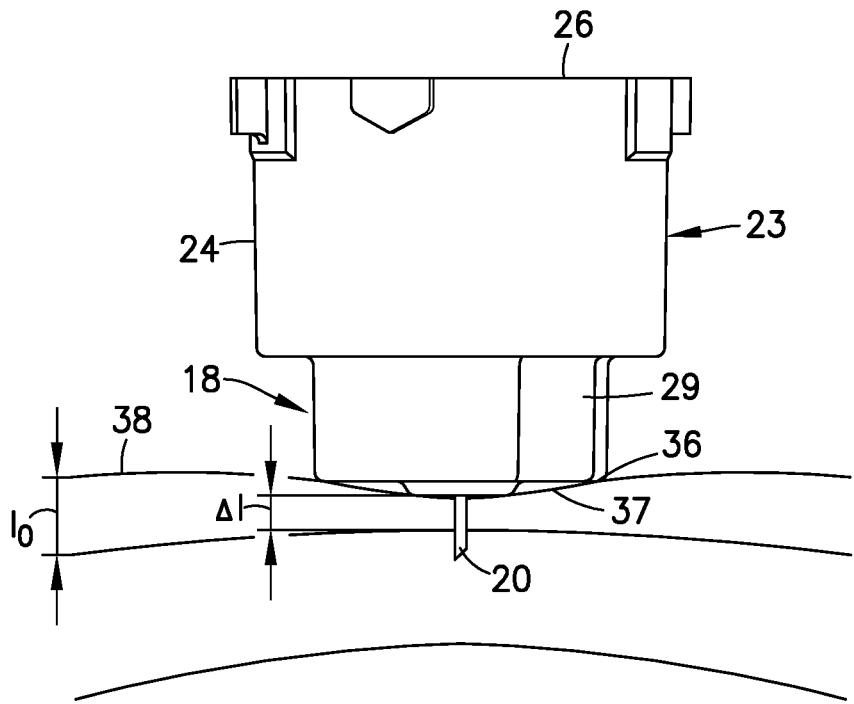
FIG. 4 is a side view of the pen needle hub in one embodiment of the pen needle showing the cannula during the initial penetration into the skin.
Figure 5:
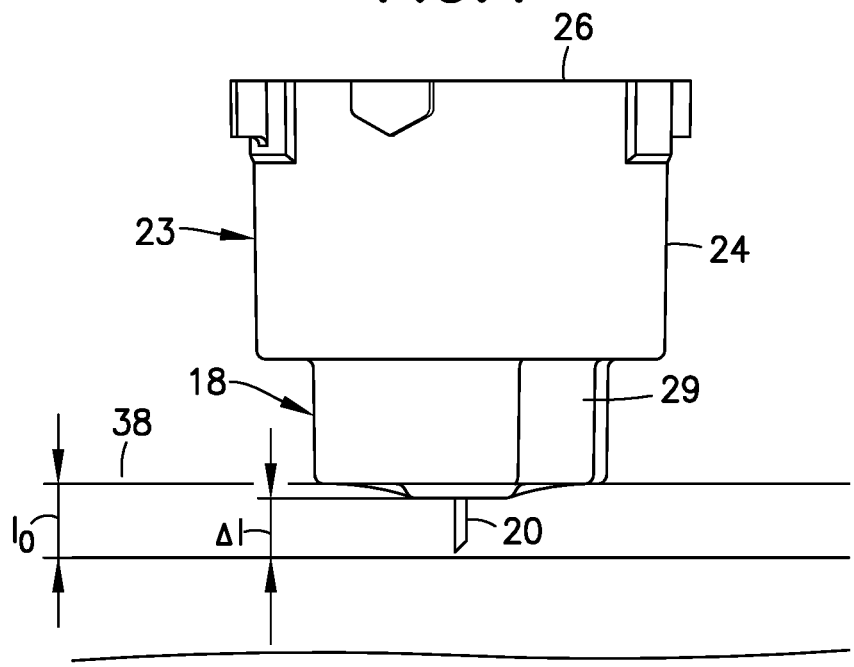
FIG. 5 is a side view of the pen needle hub of FIG. 4 showing the skin in a relaxed condition after penetration.
Figure 6:
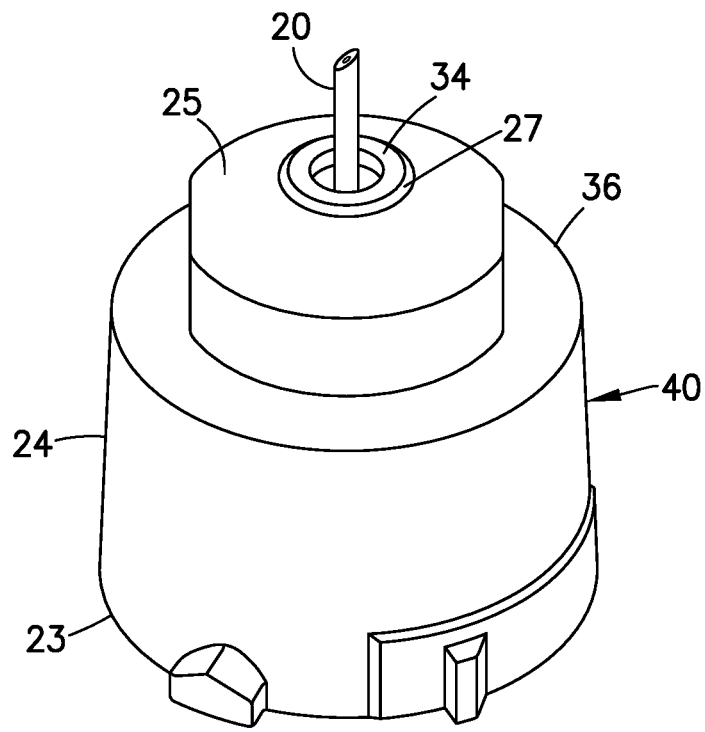
FIG. 6 is a top perspective view of the pen needle hub of FIG. 4.
Figure 8:
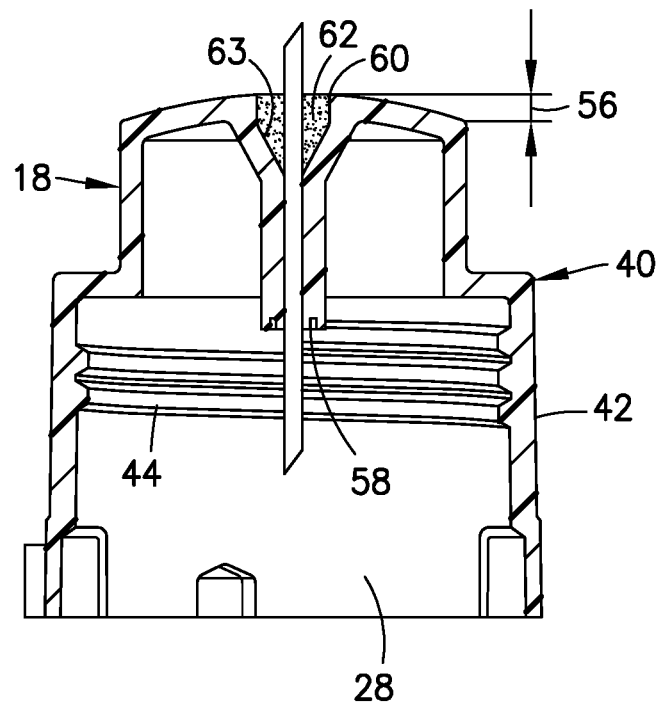
FIG. 8 is a cross sectional side view of the pen needle hub of FIG. 7.

In the embodiment of FIGS. 4, 5 and 6, the hub 18 for coupling to the delivery pen has a cylindrical shape and includes body 23 having a side wall 24 to form an open end 26. The open end 26 forms an internal cavity with internal threads as shown in the embodiment of FIG. 8 for coupling to the pen needle delivery device 150 of FIG. 3. In another embodiment, the hub may be provided with flattened sides 29, as shown in FIG. 4. The flattened sides do not impact the functionality of the curved hub face. The diameter of the hub in this instance refers the widest part of the distal-facing surface of the hub from which the cannula extends.

The hub 18 of FIGS. 4 and 5 illustrate the skin contact surface and the skin deformation by the insertion force during the insertion and penetration of the cannula by an insertion force normally applied by the patient. In the embodiment shown, the hub 18 has an inner ring 34 extending from the hub. The hub has a circular outer peripheral edge 36 defining a width or diameter of the skin contact surface 32. The inner ring 34 supporting the cannula 20 projects from the axial face 25 of the hub 20 and the peripheral edge. In this embodiment, the axial face 25 is substantially flat. The inner ring 34 has a substantially frustoconical shape or a semispherical shape with side surfaces 27 that slope from the axial distal end of the inner ring 34 to the axial face 25. In the embodiment shown, the axial face has a diameter of about 5-10 mm and typically about 7 mm to about 8.0 mm. The inner ring 34 has a height extending from the axial face of about 1 mm to about 1.5 mm and a width of about 1-4 mm.

The inner ring 34 typically has a central bore that extends through the hub for receiving and mounting the cannula. The open end of the bore has a width slightly greater than the width of the bore for receiving an adhesive to fix the cannula to the hub. The open end forms an adhesive well with a diameter of about 1.0 to 2.0 mm and typically about 1.74 mm. The adhesive is placed in the open end without projecting from the contact surface of the axial face.

As shown in FIG. 4 the initial penetration of the cannula 20 by the contact of the hub projecting from the contact surface with the skin of the patient forms depression 37 in the skin 38 and an initial cannula penetration depth. The surface of the skin then relaxes as shown in FIG. 5 so that the surface of the skin conforms substantially to the shape of the contact surface and limits the depth of penetration of the cannula 20. In FIGS. 4 and 5 the delta (Δ) refers to the distance between the axial end of the inner ring 34 and the subcutaneous layer of the skin. The invention is directed to the shape, surface area and height of the contact surface to provide control of the depth of penetration of the cannula during the insertion and penetration force being applied to the injection device.

The cannula 20 in the embodiments shown has a length of about 4.0 to 5.0 mm, typically about 4.0 mm to penetrate the skin to the desired depth for the efficient delivery of the drug and particularly insulin. The contact surface of the hub has a width and height to control the deformation and dimension of the indentation in the skin thereby controlling the depth of penetration of the cannula. The shape and dimension of the contact surface distribute the applied pressure upon full engagement to the skin surface. The contour in combination with the pressure distribution provides improve comfort to the patient. The height and surface area of the hub and the perimeter surface area influence the degree of compression and relaxation of the tissue for a given application force.

Figure 7:
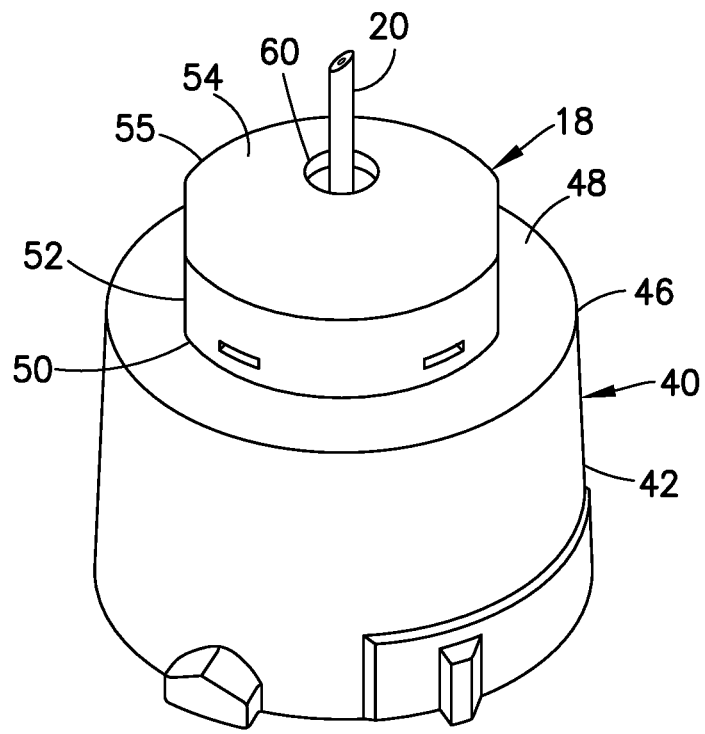
FIG. 7 is a perspective view of the pen needle hub in another embodiment of the pen needle.
Figure 9:
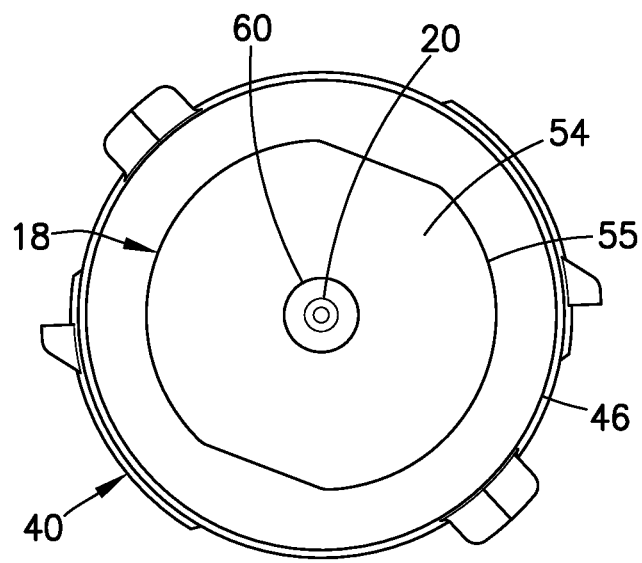
FIG. 9 is a top view of the pen needle hub of FIG. 7.

The hub 18 in the embodiment of FIGS. 7-9 has a body portion 40 having a side wall 42 with internal threads 44 for coupling with the pen delivery device. The distal end of the side wall has a peripheral edge 46 and forms a shoulder 48 extending between the peripheral edge 46 and a base 50 of a post 52 forming the distal end of the hub. The post 52 projects outward in an axial direction of hub 18 to support cannula 20. As shown in FIG. 7, post 52 extends outward from shoulder 48 and has an axial face forming a contact surface 54. In this embodiment, contact surface 54 has a continuous curved convex shape extending from peripheral edge 55 to the opening for receiving cannula 20. Contact surface 54 has a dome shape with a substantially uniform curvature forming a semispherical shape having an axial height 56 of about 0.4 to about 2.0 mm from the peripheral edge 55 to the portion around the cannula 20 and the outermost distal portion of the contact surface 54. In one embodiment, the contact surface can have a height of about 1.0 to 1.5 mm. The contact surface 54 can have a continuous curvature with a radius of curvature of about 6.0 to 10.0 mm. In one embodiment, the contact surface has a radius of curvature of about 6.0 to 8.0 mm. The curved contact surface can have surface area of about 15-100 mm². In one embodiment, the curved contact surface can have a surface area of about 50.0 to 60.0 mm². The contact surface can have a substantially flat annular portion surrounding the cannula 20 that is oriented in a plane substantially perpendicular to the axis of the cannula as shown. The flat annular portion can have a diameter of about 0.5 mm to about 2.5 mm.

The hub 18 has a centrally located passage 58 for supporting cannula 20 and a recessed open end 60 for receiving an adhesive 62 as shown in FIG. 8 to fix cannula 20 to hub 18. The recessed open end 60 can have inclined surfaces 63 forming a funnel shaped recess to receive the adhesive. In the embodiments shown, adhesive 62 fills a portion of the recessed open end 60 so that the adhesive is below the contact surface or substantially flush with the contact surface to minimize contact of the adhesive the skin and prevent or minimize alteration of the contact surface with the skin of the patient. The open end 60 can have diameter of about 1.7 to 1.8 mm.

Figure 10:
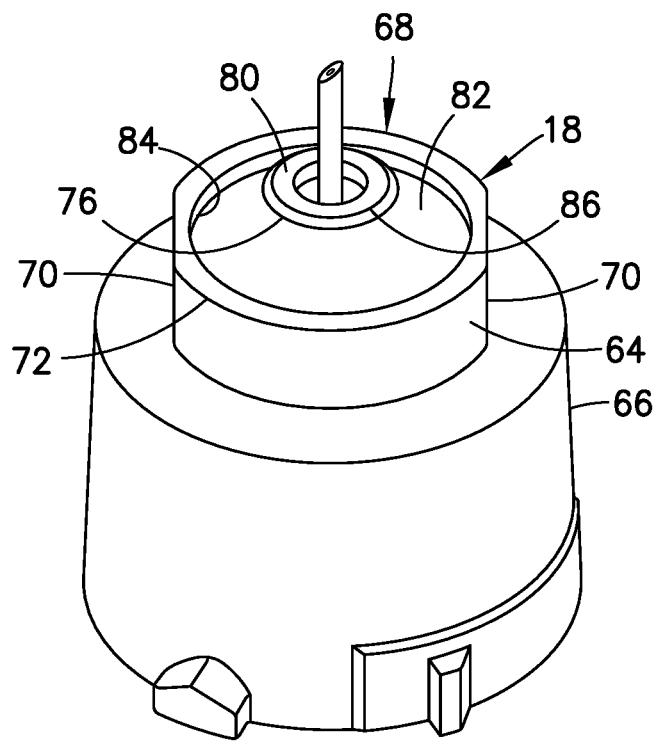
FIG. 10 is a perspective view of a pen needle in a further embodiment showing the annular recess in the contact surface.
Figure 11:
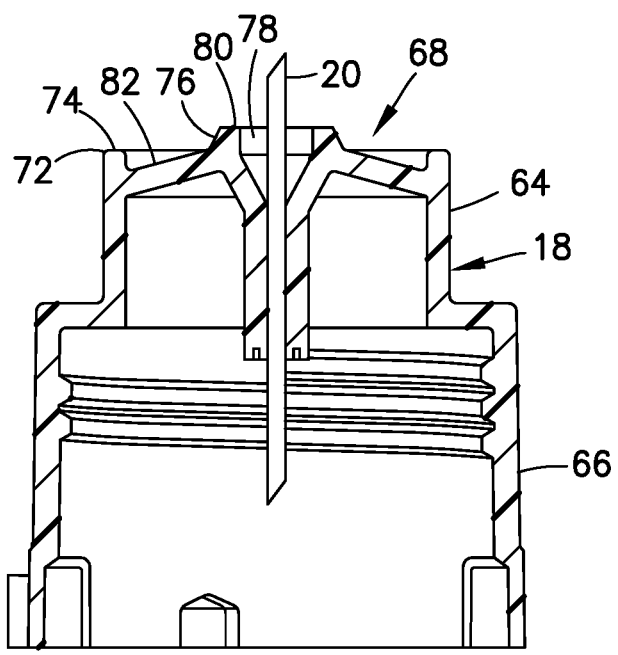
FIG. 11 is a cross sectional view of the pen needle hub of FIG. 10.

In another embodiment of the invention shown in FIGS. 10 and 11, a hub 18 has a side wall 64 extending from a base 66 with a distal contact surface 68. Side wall 64 in the embodiment shown has opposing flat portions 70 so that the contact surface 68 has a non-circular shape.

Contact surface 68 in the embodiment of FIGS. 10 and 11 is defined by an outer ring 72 forming a collar defining the peripheral edge of contact surface 68 and projecting axially outward from the distal end of the hub 18 and surrounding cannula 20. Outer ring 72 has a substantially uniform height from the distal end of the side wall 64 with a distal outer face 74 forming a peripheral edge of contact surface 68. An inner, substantially annular shaped ring 76 extends axially from contact surface 68 around the opening 78 for receiving the cannula 20 and adhesive. For clarity the adhesive is not shown in FIG. 11. Inner ring 76 has a substantially cylindrical or annular shape projecting outward and forming an inner edge of contact surface 68. Inner ring 76 has a distal outer face 80 forming part of the contact surface 68 surrounding cannula 20. Inner ring 76 and outer ring 72 define a recess 82 of contact surface 68 extending between an inner surface 84 of outer ring 72 and an inner surface 86 of inner ring 76. In one embodiment, recess 82 has a width and depth so that the bottom surface of recess 82 contacts the skin of the patient during penetration of cannula 18 to control the compression of the skin and depth of penetration shown in FIG. 12.

Contact surface 68 in the embodiment shown has a substantially convex shape with a height and width to provide the desired control of the compression of the skin and the depth of penetration of cannula 20. The distal outer face 74 of contact surface 68 as shown has an incline with respect to the axial dimension of hub 18 converging toward the outermost portion of contact surface 68 at the cannula 20 and having a substantially frustoconical shape. The distal face 80 of inner ring 76 has a similar shape inclined surface with a frustoconical shape aligned with distal outer face 74. In one embodiment distal face 80 and distal outer face 76 at aligned to form a convex shape having a radius of curvature as shown in FIG. 11.

Bottom surface of recess 82 as shown in FIG. 10 is also formed at an incline forming a frustoconical surface with a dome or semispherical shape and having a radius of curvature substantially the same as the radius of curvature of the contact surface of the inner ring and the outer ring. In the embodiment shown, the bottom surface is formed substantially concentric to the outer surface 74 of outer ring 72 and outer surface 80 of inner ring 76. The depth of recess 82 is substantially uniform and is about 0.4 to 0.6 mm relative the axial length of inner ring 72 and outer ring 76. In the embodiment shown outer ring 72 and inner ring 76 have substantially the same axial length. The depth of recess 82 relative to the width or diameter of the contact surface 68 enables the skin to deform by the insertion pressure while controlling the depth of penetration of cannula 20. In other embodiments, the recess can have a depth of about 0.5 mm to about 1.5 mm and a distal contact surface can have a width or diameter of about 5.0 to about 9.0 mm and a height of about 0.4 mm to about 0.6 mm.

Figure 12:
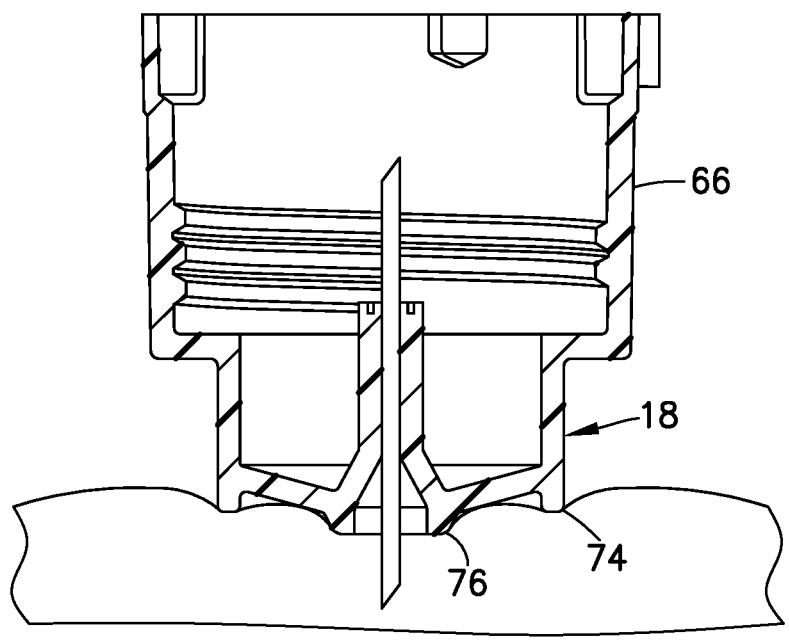
FIG. 12 is a cross sectional view showing the cannula insertion into the skin by the pen needle hub of FIG. 10.

Referring to FIG. 12 the insertion pressure applied to hub 18 causes cannula 20 to penetrate the skin to a selected depth and the contact surface 68 to contact the skin. As shown in FIG. 12, recess 82 has a depth relative to the width of contact surface 68 so that the skin contacts the bottom surface of recess 82 to provide a pressure against the skin to deform or depress the surface of the skin in a manner to control the depth of penetration of the cannula into the skin of the patient. The convex contact surface distributes the pressure across the contact area of the skin. The larger the surface area generally results in less deformation of the skin to prevent deep injections and less discomfort to the patient.

The annular recess 82 can have a radial width of about 2.0 to about 3 mm. The recess can have a volume of about 6.0 to 34.0 µl depending on the width and depth of the recess. In one embodiment the recess can have a volume of about 25.0 to 36.0 µl. The annular recess can have a radial width greater than the radial width of the inner ring and/or the outer ring. In the embodiment shown in FIGS. 10-12, the recess has a radial width that is greater than the combined width of the inner ring and the outer ring so that the bottom wall of the annular recess forms a major portion of the contact surface.

The distal contact face of the hub can have various configurations for providing the desired control for the depth of penetration of the cannula. In each embodiment, the distal contact face has a width or diameter to provide a sufficient surface area and height defined by the curvature of the contact face to minimize the depressing of the skin that can cause the cannula to penetrate the skin deeper than intended.

Figure 13:
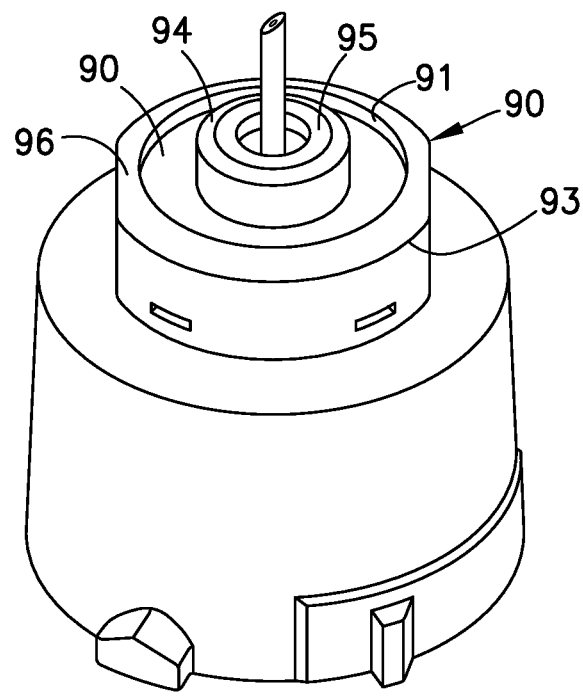
FIG. 13 is a perspective view of the pen needle hub in another embodiment of the pen needle.
Figure 14:
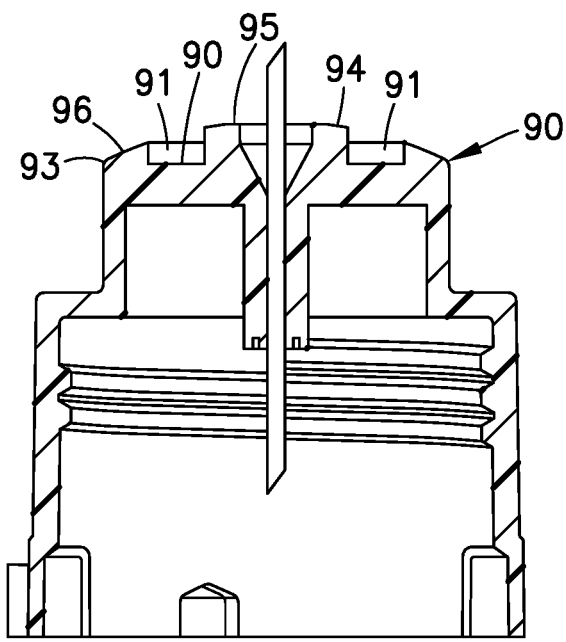
FIG. 14 is a cross sectional side view of the pen needle hub of FIG. 13.

In the embodiment of FIGS. 13 and 14 the hub 90 has a similar configuration to the embodiment of FIGS. 10-12 except for the annular recess 91 having a substantially flat bottom surface 92 that extends substantially perpendicular to the axis of the cannula. The hub 90 has an outer ring 93 and an inner ring 94 extending axially that form the recess 91 and the bottom surface 90. In this embodiment, the inner ring 94 has an axial height greater than the axial height of the outer ring 93. The inner ring 94 has an axial distal face 95 having a curved surface that slopes toward to the outer peripheral edge of the hub 90. The outer ring 93 has an axial distal face 96 having a curved surface that also slopes radially outward toward the peripheral edge.

The axial distal face 96 of the outer ring 93 and the outer distal face 95 of the inner ring 94 form the skin contact surface and define the width and height of the contact surface. The inner ring 94 extends in an axial direction a distance greater than the outer ring 93 to define the height of the contact surface. As in the previous embodiments, the contact surface can have a height of about 0.5 to about 1.50 mm and a width of about 6.0 to 7.0 mm.

The axial distal face 96 of the outer ring 93 and the axial distal face 95 of the inner ring 94 in the embodiment shown have a round, curved surface to define a radius of curvature of the contact surface in a manner similar to the embodiment of FIGS. 10-12. The annular recess in this embodiment has a depth that can receive the skin as the skin deforms when the insertion pressure is applied although the skin typically does not contact the bottom surface of the recess.

Figure 15:
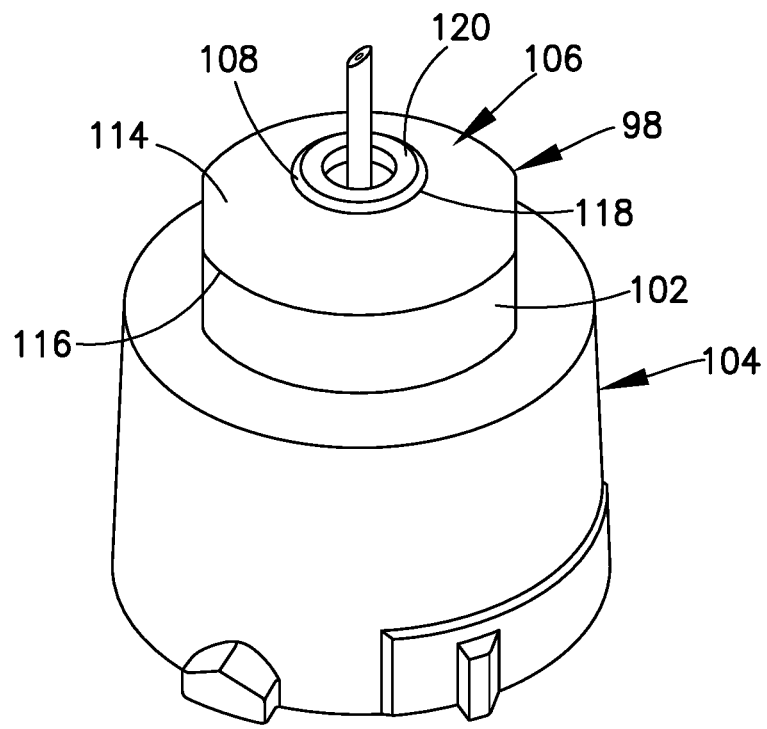
FIG. 15 is a perspective view of the pen needle in a further embodiment of the pen needle hub.
Figure 16:
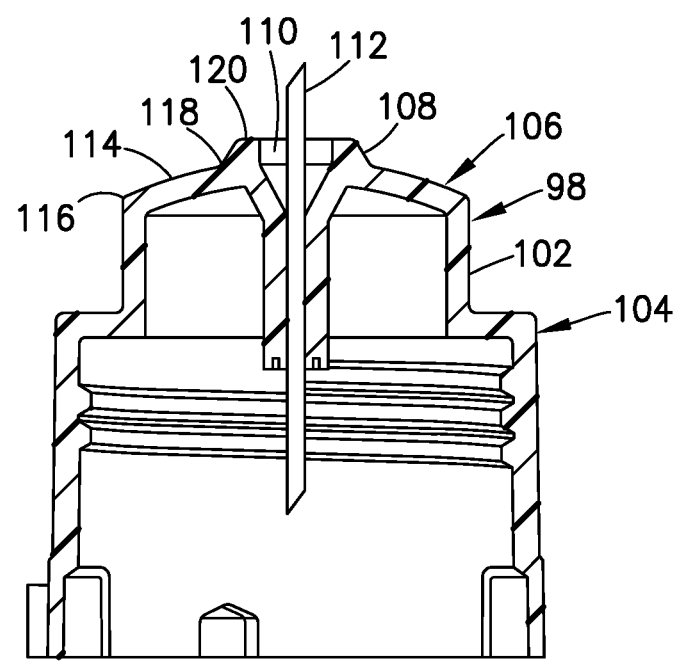
FIG. 16 is a cross sectional side view of the pen needle hub of FIG. 15.

In another embodiment shown in FIGS. 15 and 16 the hub 98 is defined by a substantially cylindrical side wall 102 extending axially from the base 104. The hub 100 has a distal face 106 forming a skin contact surface. The distal face can have a width of about 6.0 to about 8.0 mm and typically about 7.0 mm. As shown in FIG. 16, the distal face 106 has an inner ring 108 extending axially from an inner portion of the distal face 106 and defining the center opening 110 for the cannula 112. In the embodiment shown the inner ring 108 has an axial length of about 0.4 to about 1.0 mm and a diameter of about 2.0-3.0 mm and a surface area of about 3.0-5.0 mm.

The distal face 106 has an inclined distal surface 114 with a substantially dome or semispherical shape extending between the peripheral edge 116 and the base 118 of the inner ring 108. The inclined distal surface 114 has a radius of curvature of about 6.0 to about 9.0 mm to form a continuous arc and radius of curvature. The inner ring 108 has an annular distal face 120 that is inclined to complement the incline and curvature of the distal surface 114.

In one embodiment the distal face 120 of the ring 108 has a semispherical shape with a radius of curvature substantially the same as the radius of curvature of the distal surface 114 so that the surfaces are concentric. The height of the inner ring 108 is selected to complement the width of the distal face so that the skin contacts the inner ring 108 and at least a substantial portion of the surface of the inclined distal surface during penetration of the cannula to control the depth of depression of the skin and the depth of penetration of the cannula. The contact surface can have a surface area of 30.0 to 50.0 mm². The inclined surface 114 can have a surface area of about 31.0 to 33.0 mm², The distal face 120 of the inner ring 94 can have a surface area of about 1.0 to about 3.0 mm² and a diameter of about 2.0 to about 2.5 mm.

Figure 17:
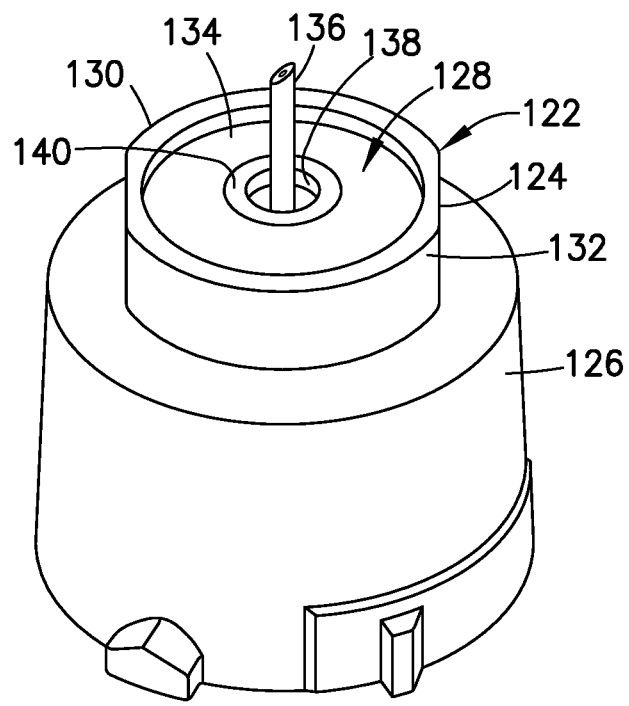
FIG. 17 is a perspective view of the pen needle hub in another embodiment of the pen needle.
Figure 18:
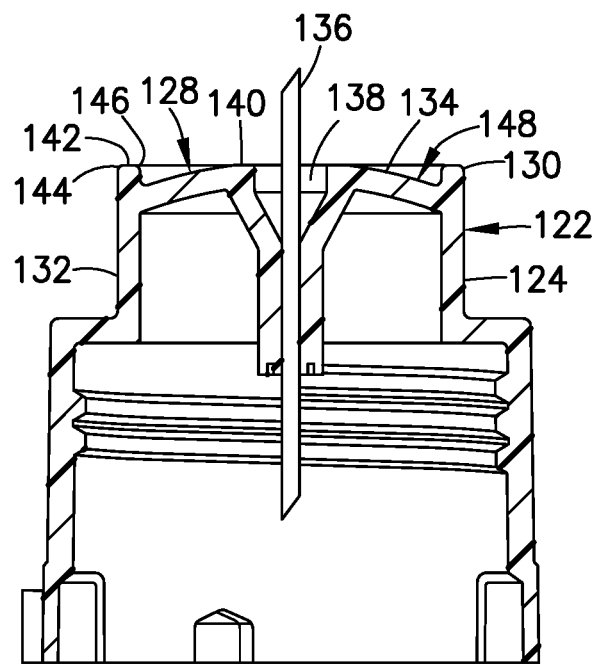
FIG. 18 is a cross sectional side view of the pen needle hub of FIG. 17.

In the embodiment of FIGS. 17 and 18, the hub 122 has a cylindrical side wall 124 extending axially from the base 126. The hub 122 has a distal face 128 forming the skin contact surface. A continuous outer ring 130 extends axially from the side wall 124 to define a peripheral edge 132 of the distal face 128. In the embodiment shown, the outer ring 130 extends in an axial direction with a height of about 0.4 to about 0.6 mm. The inner and outer surfaces of the outer ring are substantially concentric and extend in an axial direction with respect to an axial dimension of hub 122. The flat portion can have a radial width of about 0.5 mm to about 2.5 mm.

The distal face 128 is formed by a continuous inclined surface 134 forming a substantially continuous dome or semispherical shape with a radius of curvature of about 6.0 to about 10.0 mm. The inclined surface 134 forms a continuous surface surrounding the cannula 136. In the embodiment of FIGS. 17 and 18, hub 122 has a central opening 138 for receiving the cannula 136. The distal face 128 has a substantially flat annular shaped portion 140 surrounding the opening 138 and oriented in a plane substantially perpendicular to the axis of the cannula and the axis of the hub. The flat annular portion 140 can have a radial width extending between the inner edge of the inclined surface 134 and the opening 138 substantially equal to the width of the distal surface 142 of the outer ring 130.

The distal surface 142 of outer ring 130 as shown in FIG. 17 is inclined radially outward with respect to the axis of the side wall 124. The distal surface 142 has an outer peripheral edge 144 spaced axially from an inner edge 146, In this embodiment the inner edge 146 is in a plane with the flat inner portion 140 that is substantially perpendicular to the axis of the cannula to define the distal face of the hub. The outer ring 130 defines a recess 148 in the distal face having a depth so that the inclined surface contacts the skin during the penetration of the cannula 136. The recess 148 can have a volume of about 6.0 to 7.0µl As in the previous embodiments, the distal face for contacting the skin during penetration and insertion of the cannula has a width or diameter in its widest point of about 6.0 to about 8.0 mm and the recess formed by the outer ring 130 has a depth of about 0.4 to about 0.6 mm. In other embodiments, the recess can have a depth of about 1.0 to about 1.5 mm.

Figure 19:
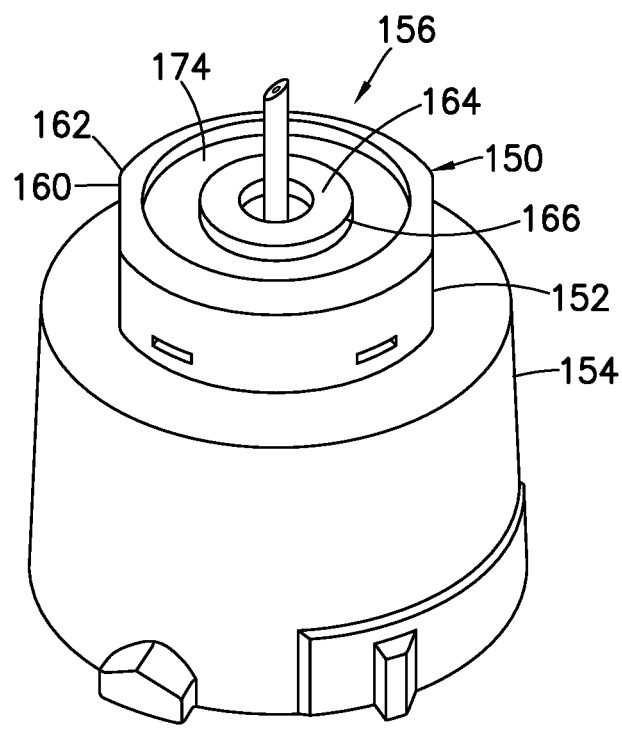
FIG. 19 is a perspective view of the pen needle hub in a further embodiment of the pen needle.
Figure 20:
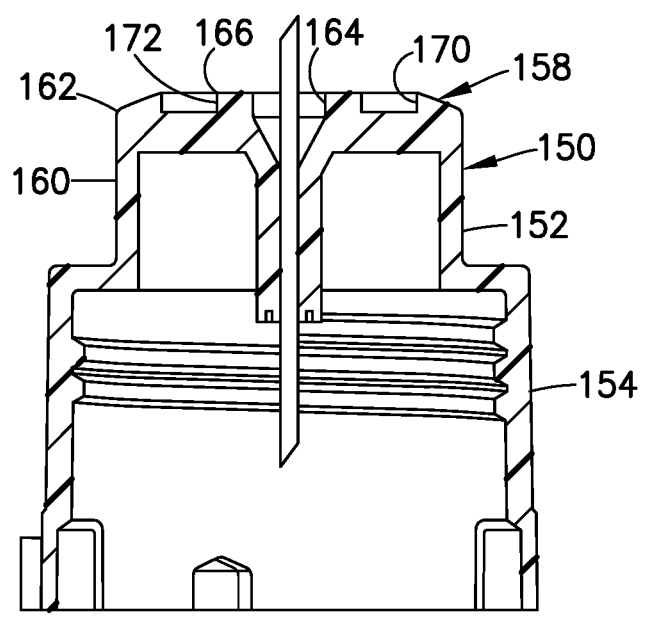
FIG. 20 is a cross sectional side view of the pen needle hub of FIG. 19.

In a further embodiment shown in FIGS. 19 and 20 the hub 150 has side wall 152 extending from a base 154 and a distal face 156 for contacting the skin of the patient during insertion of the cannula 158. The distal face 156 includes an outer ring 160 extending axially from a peripheral edge 162 and an axially extending inner ring 164 forming an inner edge 166. As shown in FIG. 19, the outer ring as a distal face formed in the same plane as a distal face of the inner ring 164.

Figure 21:
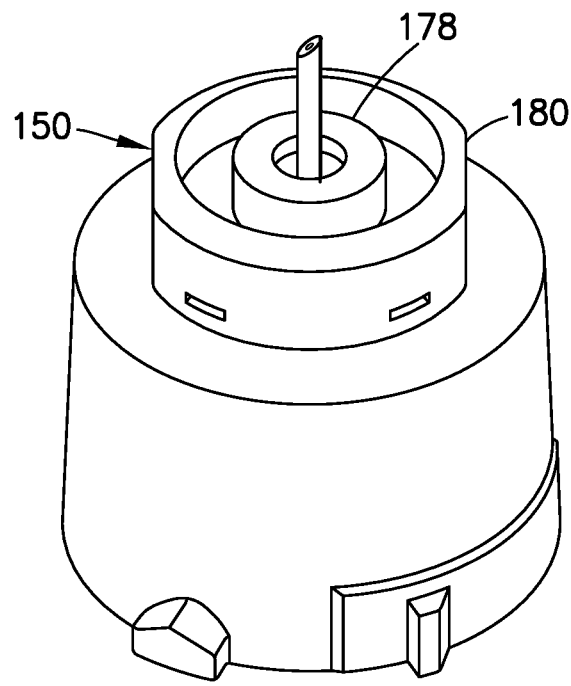
FIG. 21 is a perspective view of the pen needle in another embodiment of the pen needle hub.
Figure 22:
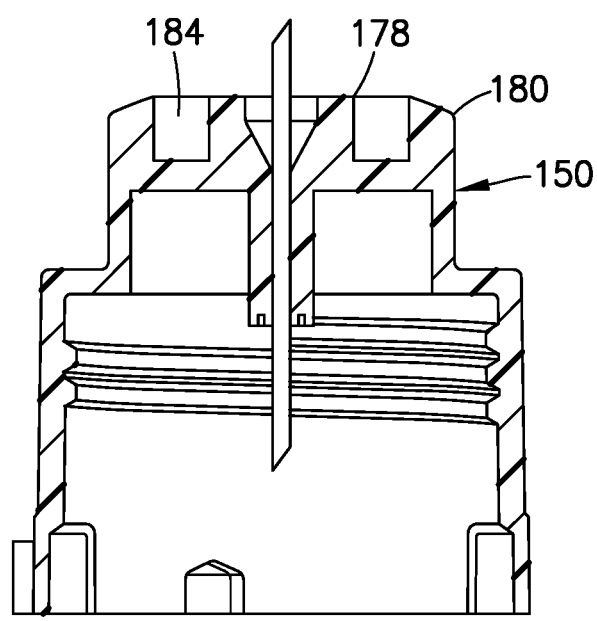
FIG. 22 is a cross sectional side view of the pen needle hub of FIG. 21.

The outer ring 160 is formed by a cylindrical outer surface extending from the side wall and a substantially parallel inner surface 170. The distal face 156 in the embodiment shown is formed at an incline to slope radially outward from the center of the hub. The inner ring 164 has in substantially cylindrical inner surface 172 parallel with the inner surface of the outer ring 160. An annular recess 174 is formed between the outer ring 160 and the inner ring 164. In the embodiment shown, the recess 174 has depth of about 0.4 to about 0.6 mm, a volume of about 7.0 µl and a width or radius of about 1.0 to 1.5 mm. As in the previous embodiments, the recess has a width and a depth to enable the skin to contact the bottom face of the recess forming a central portion of the distal face forming the contact surface. The contact surface has a width of about 6.0 to 8.0 mm. Another embodiment shown in FIGS. 20 and 21 is substantially the same as in FIGS. 19 and 20 except for inner ring 178 and the outer ring 180 of the hub 182 forming a recess 184 having a depth of about 1.5 to 2.0 mm and a well volume of about 11 μl.

Figure 23:
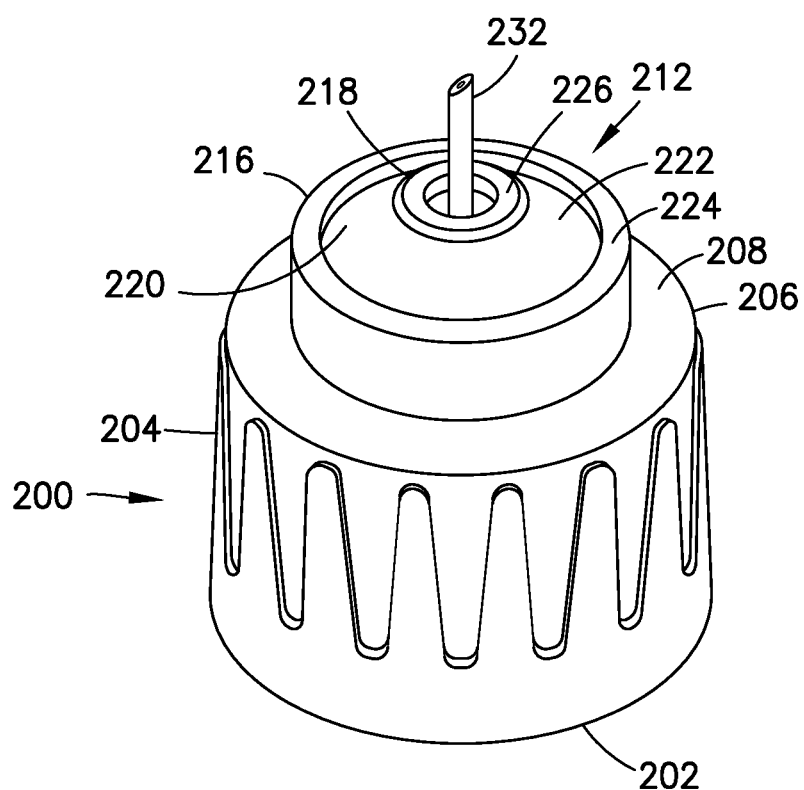
FIG. 23 is a perspective view of a further embodiment of the pen needle hub.
Figure 24:
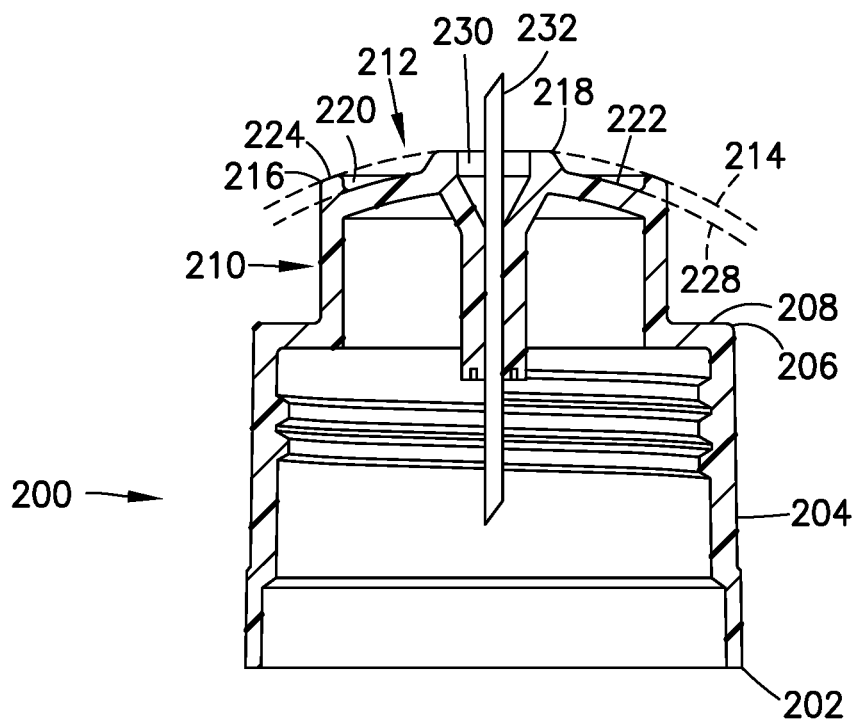
FIG. 24 is a cross sectional side view of the pen needle hub of FIG. 23.

FIG. 23 and FIG. 24 show another embodiment of a needle hub 200 for attaching to a delivery pen as in the previous embodiments. The hub 200 has a base 202 with an outer wall 204 having an open bottom end and internal threads 204 for coupling to the delivery device. The wall 204 has a distal end 206 joined with an inwardly extending shoulder 208. A substantially cylindrical shaped wall 210 extends axially from the shoulder 208. The wall 210 has an axial distal face 212 defining a skin contact surface for contacting the skin of a patient during use.

The contact surface defined by the distal face 212 has substantially convex shaped forming a dome or semispherical shape depicted by line 214 in FIG. 24. The distal face 212 can have a radius of curvature of about 6 to 12 mm. In one embodiment, the distal face 212 has a radius of curvature of about 6 to 9 mm and typically about 7-8 mm. The radius of curvature can be at least equal to the diameter of the contact surface.

The post 210 as shown in FIGS. 23 and 24 has a substantially cylindrical shape formed by a side wall 214 extending from the shoulder 208. The distal face 212 defining the skin contact surface also has a substantially circular shape when viewed from the top end shown in FIG. 24. The distal face 212 is formed by an annular outer ring 216, an annular inner ring 218 and an annular shaped recess 220 forming a well between the outer ring 216 and the inner ring 216.

The outer ring 216 and the inner ring 218 in the embodiment shown have a height extending from the bottom wall 222 of the recess 220 to define the depth of the recess. The outer ring and inner ring have the same axial length so that the recess 220 has a substantially uniform and continuous depth extending between the outer radial edge and the inner edge of the recess. The outer ring 216 has an axial annular surface 224 that is inclined with respect to the axial dimension of the hub to form the convex distal face 212. The incline of the axial face 224 conforms to the radius of curvature of the distal face 212.

The inner ring 218 in the embodiment shown also has an axial face 226 with a curvature corresponding substantially to the curvature of the axial face 224 of the outer ring. The axial face 224 and axial face 226 are aligned along the curvature of the distal face 212 indicated by line 214. In the embodiment shown, the axial face 224 and axial face 226 are substantially the same width with substantially the same radius of curvature. The bottom wall 222 of recess 220 has a radius of curvature that is substantially the same as the radius of curvature of the distal face 212 as indicated by line 228 so that the contour of the bottom wall 22 is substantially parallel or concentric to line 214. The curvature of the distal face 212 defines a height of about 0.5 to 2.0 mm as measured from the outer edge of the outer ring to the axial face of the inner ring. In one embodiment the distal face 212 can have a height of about 1.0 to 1.5 mm The inner ring 218 defines a central opening 230 for receiving and mounting a cannula 232 as in the previous embodiments. The opening 230 can have a diameter of 0.5 to 3.0 mm for securing the cannula to the hub. In one embodiment, the distal face 212 forming the skin contact surface can have a diameter of about 6.0 to 8.0 mm. The radial dimension or width of the annular recess 220 can be equal to the combined radial width of the inner ring and the outer ring. In the embodiment shown, the annular recess has a radial width about twice the radial width of each of the inner and outer rings. The axial face 224 and axial face 226 each can have radial width of about 0.3 to 0.7 mm and the annular recess 220 can have a radial width of about 0.6 to 1.4 mm. The annular recess can have a depth of about 0.3 to about 0.7 mm and typically about 0.5 mm. The cannula can have an axial length of about 4 to 5 mm. The combination of the cannula length with the distal contact surface having a radial diameter and height as defined herein provide control of the depth of penetration of the cannula during insertion into the patient. The width and curvature of the distal face provide the controlled depression of the skin to reduce the incidence of that cannula penetrating the skin to a depth deeper than desired during the drug delivery.

In various embodiments, the inner ring can have a diameter of about 2.0-4.0 mm and generally about 2.5-3.5 mm with a surface area of about 3-5 mm$^2$. The inner ring can have a height of about 1.0-1.5 mm as measured from the outer periphery of the contact surface. The ratio of the diameter (D) of the inner ring to the height of the inner ring can range from about 2:1 to about 4:1 and generally about 2.5:1 to 3:1. The larger ratio provides a greater surface area that provides increased comfort to the patient and greater control of the insertion depth.

The depth of the recess can vary depending on the desire depth of penetration by the cannula. The radial dimension of the annular recess is typically greater than the radial dimension of the inner and outer rings. In the embodiment shown the radial dimension of the annular recess is greater than the combined radial dimension of the inner and outer rings. Generally the greater the depth of the recess the small contact surface area of the distal face and more deformation of the skin surface enabling deeper penetration by the cannula. The curvature of the distal surface of the inner and outer rings forming the contact surface can also vary. In the embodiments illustrated, the distal surface of the inner and other rings are substantially the same. In other embodiments, the distal surface of the inner ring can have a radius of curvature that is greater or smaller than the radius of curvature of the outer ring. In further embodiments, the distal surfaces of the inner ring and/or the outer ring can be substantially flat and formed in a plane substantially perpendicular to the axis of the cannula.

The hub device is suitable for use in a method of reducing shallow injections and for injecting a drug to a patient. The method includes providing a pen body having a medication compartment and a distal end configured for receiving a pen needle. The pen needle includes a hub having base with a recess on a proximal side for receiving and coupling to the pen body. As distal face and an opening extends between the proximal side and the distal face. The distal face of the hub has a diameter greater than about 3.0 mm. At least a portion of the distal face has a convex surface with a radius of curvature of about 3.0 to 16.0 mm. It has been found that a hub having a width of about 6.0 to 8.0 mm and a radius of curvature of about 12.0 to 16.0 mm provides a desired depth of penetration. In various embodiments the radius of curvature of the distal face forming the skin contact surface can be about one to one and a half times the diameter of the distal surface 212 to form a small curvature and a height of about 0.5 mm. A cannula is received in the opening in the hub and has a beveled end for injecting into the subject's skin, and a proximal end for positioning in the medication compartment of the pen body. The cannula is inserted into the subject's skin where the convex surface contacts the skin to limit the depressing and deforming the surface of the skin to control the depth of penetration of the cannula.

The above description of the preferred embodiments is not to be deemed as limiting the invention, which is defined by the appended claims. The disclosure is intended to enable the artisan of ordinary skill to practice variants of the invention described without departing from the scope of the invention. Numerical limitations herein, in the specification and in the claims, are understood to be limited by the modifier "about," such that minor departures yielding equivalent results is within the scope of the invention. Features or dependent claim limitations disclosed in connection with one embodiment or independent claim may be combined in another embodiment or with a different independent claim without departing from the scope of the invention.

The invention claimed is:

1. A pen needle comprising,
a hub having a recess on a proximal side for receiving a medication pen body and a distal end;
a cannula received in said hub and extending from said distal end of said hub, said cannula having a distal end for injection into a subject's skin, and a proximal end for positioning in a medication compartment of the pen body;
wherein the hub has a distal surface at said distal end forming a convex skin contact surface when the cannula penetrates the subject, the skin contact surface having a diameter greater than 3.0 mm and 10 mm or less, said skin contact surface having an outer peripheral surface at an outer peripheral edge of said distal surface, an inner annular surface surrounding said cannula and projecting axially from said distal surface and spaced axially from the outer peripheral surface, and a convex curved portion extending between said outer peripheral surface and said inner annular surface where said inner annular surface projects axially from a surface of said curved portion, and said curved portion having a radius of curvature in a range of 3.0 mm to 16.0 mm.

2. The pen needle according to claim 1, wherein said curved portion of the distal surface has a radius of curvature in range of 6.0 mm to 9.0 mm.

3. The pen needle according to claim 1, wherein the inner annular surface has a flat portion adjacent the cannula having a diameter of 0.5 mm to 2.5 mm, the curved portion extending on all sides of the flat portion to said outer peripheral edge of the distal surface.

4. The pen needle according to claim 1, wherein said curved portion surface has a substantially continuous convex surface extending between the outer peripheral outer edge of said distal surface and said inner annular surface.

5. The pen needle according to claim 1, wherein said inner annular surface has a substantially planar surface surrounding said cannula and extending in a plane substantially perpendicular to an axis of said cannula, and where said curved portion forms a continuous convex surface extending between the outer peripheral edge of said distal surface and a peripheral outer edge of said planar surface.

6. The pen needle according to claim 1, wherein said cannula has a length of 4.0 to 5.0 mm and said distal surface has a width of 5.0 to 10.0 mm.

7. The pen needle according to claim 1, wherein said inner annular surface forms an inner ring extending axially from said curved portion and has an axial distal face with a radial width to contact the surface of the skin during insertion of the cannula into the skin of the subject.

8. The pen needle according to claim 1, wherein said curved portion forms an annular shaped recessed portion extending between said outer peripheral surface and said inner annular surface, wherein said inner annular surface and outer peripheral surface of said distal surface form a continuous curve having a radius of curvature of 6.0 to 12.0 mm.

9. The pen needle according to claim 8, wherein said recessed portion has a continuous convex surface with a radius of curvature of 6.0 to 12.0 mm wherein said convex surface is concentric with said inner distal surface and outer distal surface.

10. The pen needle according to claim 8, wherein said recessed portion has a depth of 0.4 to 1.0 mm, said distal surface has a width of 5.0 to 10.0 mm and a height of 1.0 to 1.5 mm between the outer peripheral edge of said distal surface and said inner annular surface.

11. The pen needle of claim 1, wherein said inner annular surface forms an annular inner ring extending axially from said distal surface and is spaced axially from said curved surface.

12. The pen needle of claim 11, wherein said inner annular surface is spaced axially from said outer peripheral surface a distance of 0.4 to 2.0 mm.

13. The pen needle of claim 11, wherein said outer peripheral surface forms an annular outer ring extending axially from said curved portion, and where said curved portion defines an annular recess extending between said inner annular ring and said outer annular ring, said annular recess having a depth to contact the skin during injection of the cannula into the subject.

14. The pen needle of claim 13, wherein an axial face of said annular outer ring is aligned in a plane of an axial face of said inner annular ring.

15. The pen needle of claim 14, wherein said annular inner ring is spaced axially from said outer annular ring, and said inner annular surface forms an inner annular ring extending axially from said curved portion, said annular outer ring and said annular inner ring having an axial face forming a convex surface with a radius of curvature of 6.0 mm to 12.0 mm.

16. The pen needle of claim 14, wherein said inner axial ring has an axial face with a radial width of about 0.3 mm to about 0.7 mm, the outer annular ring has an axial face with a radial width of about 0.3 mm to about 0.7 mm, and said annular recess has a radial width of about 0.6 mm to about 1.4 mm.

17. A medication pen, comprising:
a pen body having a medication compartment and a distal end for receiving and coupling to a pen needle as defined in claim 1.

18. The medication pen according to claim 17, wherein said curved portion forms an annular shaped recessed portion extending between said outer peripheral surface edge and said inner annular surface, wherein said inner annular surface and outer peripheral surface of said distal surface are aligned in a continuous curve having a radius of curvature of 6.0 to 12.0 mm.

19. The medication pen according to claim 18, wherein said recessed portion has a continuous convex surface with a radius of curvature of 6.0 to 12.0 mm wherein said convex surface is concentric with said inner distal surface and outer distal surface.

20. The medication pen according to claim 19, wherein said recessed portion has a depth of 0.4 to 1.0 mm, said distal face has a width of 5.0 to 10.0 mm and a height of 1.0 to 1.5 mm between the outer peripheral edge of said distal surface and said inner annular surface.

21. The medication pen according to claim 17, wherein said inner annular surface extends in a plane substantially perpendicular to an axis of said cannula, and where said curved portion forms a continuous convex surface extending between the outer peripheral edge of said hub and a peripheral outer edge of said inner annular surface.

22. A pen needle comprising:
  a hub having a proximal end for receiving a medication pen body and a distal end;
    a cannula received in said hub and extending from said distal end of said hub, said cannula having a distal end and a proximal end;
    wherein the hub has a distal surface at said distal end forming a skin contact surface when the cannula penetrates the subject, the skin contact surface having a diameter greater than 3.0 mm and 10 mm or less, said skin contact surface having an outer peripheral surface at an outer peripheral edge of said distal surface, an inner annular surface surrounding said cannula and spaced axially from the outer peripheral surface, and a curved portion extending between said outer peripheral surface and said inner annular surface, and said curved portion having a radius of curvature in a range of 3.0 mm to 16.0 mm;
  said hub further comprising a body having a distal end and a proximal end with an opening for coupling with a medication delivery pen device, said body having a sidewall with an outer surface with an outer dimension, and an inner surface with a first section at a distal end with a first dimension and a second section at a proximal end at said opening with a second dimension greater than said first dimension of said inner surface;
  a tower extending from said body and having a sidewall with an outer surface, an inner surface, and having an outer dimension less than said outer dimension of said body, and an end wall defining said skin contact surface; and
  a post extending from an inner surface of said end wall and extending toward said open end of said body, said post configured for supporting said cannula extending from said end wall of said tower.

23. The pen needle of claim 22, wherein said second section of said inner surface of said sidewall forms an annular recess at said opening of said proximal end.

24. The pen needle of claim 23, wherein said second section of said sidewall has internal threads for coupling with the medication delivery device, and where said annular recess is spaced from said internal threads.

25. The pen needle of claim 24, wherein said inner surface of said side wall has an inclined shoulder extending between said first section and said second section.

26. A pen needle comprising;
  a hub having a proximal end for receiving a medication pen body and a distal end;
    a cannula received in said hub and extending from said distal end of said hub, said cannula having a distal end and a proximal end;
    wherein the hub has a distal surface at said distal end forming a skin contact surface when the cannula penetrates the subject, the skin contact surface having a diameter greater than 3.0 mm and 10 mm or less, said skin contact surface having an outer peripheral surface at an outer peripheral edge of said distal surface, an inner annular surface surrounding said cannula and spaced axially from the outer peripheral surface, and a curved portion extending between said outer peripheral surface and said inner annular surface, and said curved portion having a radius of curvature in a range of 3.0 mm to 16.0 mm,
    wherein said inner annular surface defines a raised inner ring having an axial face, said outer peripheral surface defines a raised outer ring having an axial face, said curved portion forms an annular recess extending between said outer peripheral surface and said inner annular surface, and where said annular recess has a bottom surface with said radius of curvature corresponding to a radius of curvature of said axial face of said raised inner ring and said axial face of said raised outer ring.

* * * * *